(12) United States Patent
Bradway et al.

(10) Patent No.: US 10,463,517 B2
(45) Date of Patent: Nov. 5, 2019

(54) CONTROLLED EXPANSION STENT GRAFT DELIVERY SYSTEM

(71) Applicant: Cook Medical Technologies LLC, Bloomington, IN (US)

(72) Inventors: Ryan Bradway, Tacoma, WA (US); Charles Baxter, West Lafayette, IN (US); Jarin Kratzberg, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 191 days.

(21) Appl. No.: 15/822,760

(22) Filed: Nov. 27, 2017

(65) Prior Publication Data

US 2018/0200093 A1   Jul. 19, 2018

Related U.S. Application Data

(60) Provisional application No. 62/446,688, filed on Jan. 16, 2017.

(51) Int. Cl.
*A61F 2/95* (2013.01)
*A61M 25/01* (2006.01)
(Continued)

(52) U.S. Cl.
CPC .................. *A61F 2/95* (2013.01); *A61F 2/07* (2013.01); *A61F 2/243* (2013.01); *A61F 2/89* (2013.01);
(Continued)

(58) Field of Classification Search
CPC .... A61F 2/07; A61F 2/89; A61F 2/243; A61F 2/966; A61F 2/95; A61F 2002/9511; A61F 2002/9665; A61F 2002/9517; A61F 2002/9534; A61F 2002/9522; A61M 25/0136
See application file for complete search history.

(56) References Cited

U.S. PATENT DOCUMENTS 5,776,142 A    7/1998  Gunderson
6,168,616 B1 *  1/2001  Brown, III ................ A61F 2/86
                                                        606/108
(Continued)

FOREIGN PATENT DOCUMENTS

EP    2471498    7/2012
EP    2832322    2/2015
(Continued)

OTHER PUBLICATIONS

European Patent Office, European Search Report for Application No. 17208215.8, Published May 25, 2018, Munich Germany.

*Primary Examiner* — Phong Son H Dang
(74) *Attorney, Agent, or Firm* — Liell & McNeil

(57) ABSTRACT

A controlled expansion stent graft delivery system has an adjustment configuration in which a retractable sheath is at a retracted position out of contact with a stent graft, but expansion of the stent graft is controlled by a control tether, which has a middle segment wrapped around a fabric tube of the stent graft. The stent graft changes diameter responsive to a tension level in the control tether. At least one of an orientation and a position of the stent graft may be adjusted during controlled expansion via the control tether.

20 Claims, 4 Drawing Sheets

(51) Int. Cl.
    *A61F 2/24*     (2006.01)
    *A61F 2/89*     (2013.01)
    *A61F 2/07*     (2013.01)
    *A61F 2/966*    (2013.01)

(52) U.S. Cl.
    CPC ......... *A61F 2/966* (2013.01); *A61M 25/0136* (2013.01); *A61F 2002/9511* (2013.01); *A61F 2002/9517* (2013.01); *A61F 2002/9522* (2013.01); *A61F 2002/9534* (2013.01); *A61F 2002/9665* (2013.01)

(56)         References Cited

U.S. PATENT DOCUMENTS

| | | | |
|---|---|---|---|
| 7,335,224 B2 * | 2/2008 | Ohlenschlæger | A61F 2/07 623/1.11 |
| 7,468,070 B2 * | 12/2008 | Henry | A61F 2/95 623/1.12 |
| 7,780,717 B2 | 8/2010 | Ducke et al. | |
| 8,663,305 B2 | 3/2014 | Argentine | |
| 8,834,550 B2 * | 9/2014 | Leanna | A61F 2/95 623/1.11 |
| 8,968,380 B2 * | 3/2015 | Nimgaard | A61F 2/95 623/1.11 |
| 9,149,358 B2 * | 10/2015 | Tabor | A61F 2/2412 |
| 9,173,755 B2 * | 11/2015 | Berra | A61F 2/07 |
| 9,198,786 B2 * | 12/2015 | Moore | A61F 2/07 |
| 9,220,617 B2 * | 12/2015 | Berra | A61F 2/07 |
| 2003/0050684 A1 | 3/2003 | Abrams et al. | |
| 2008/0294234 A1 | 11/2008 | Hartley et al. | |
| 2009/0054966 A1 | 2/2009 | Rudakov et al. | |
| 2011/0022149 A1 | 1/2011 | Cox et al. | |
| 2012/0172965 A1 * | 7/2012 | Kratzberg | A61F 2/962 623/1.12 |
| 2014/0052232 A1 | 2/2014 | Cragg et al. | |
| 2018/0311030 A1 * | 11/2018 | Bradway | A61F 2/966 |
| 2019/0209318 A1 * | 7/2019 | Zhang | A61F 2/2436 |
| 2019/0231526 A1 * | 8/2019 | Alkhatib | A61F 2/2436 |

FOREIGN PATENT DOCUMENTS

| | | |
|---|---|---|
| EP | 2471498 | 7/2017 |
| EP | 3272319 | 1/2018 |
| WO | 2009105176 | 8/2009 |

* cited by examiner

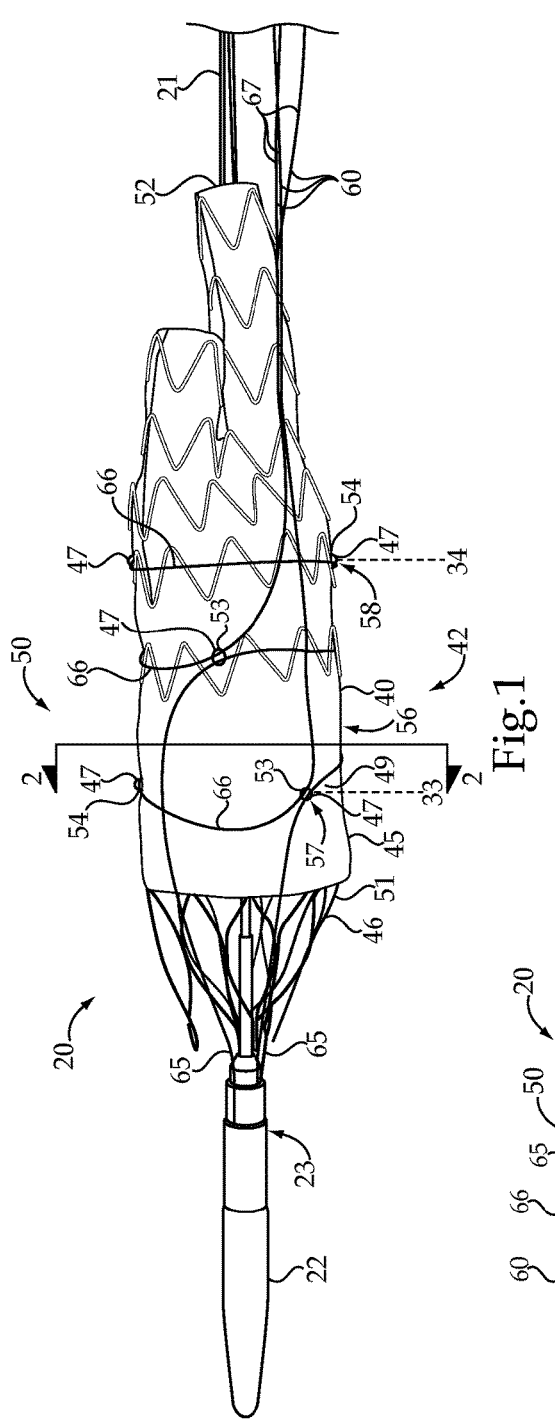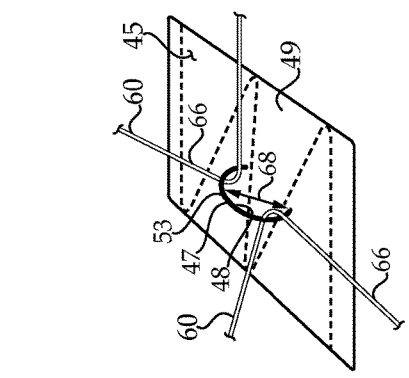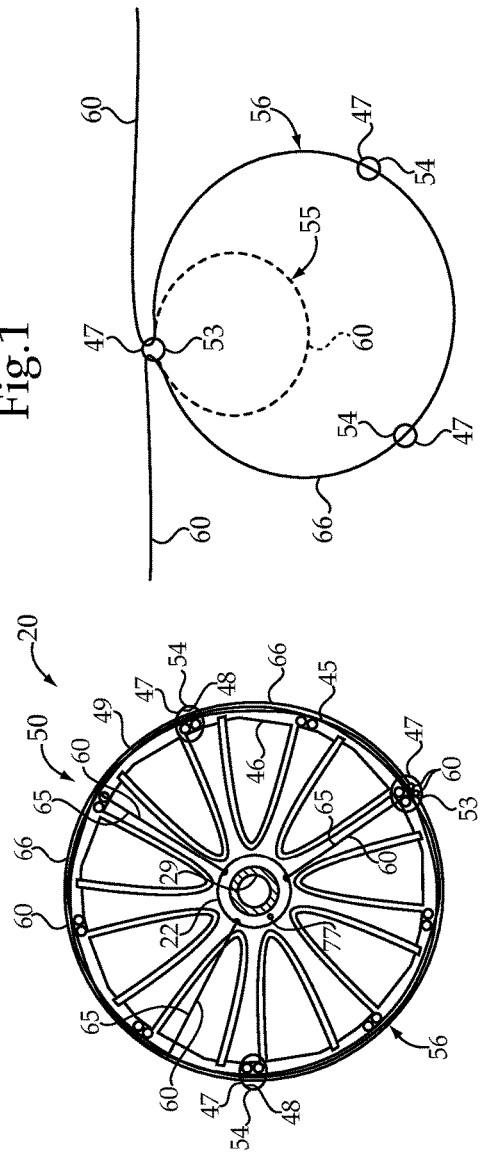

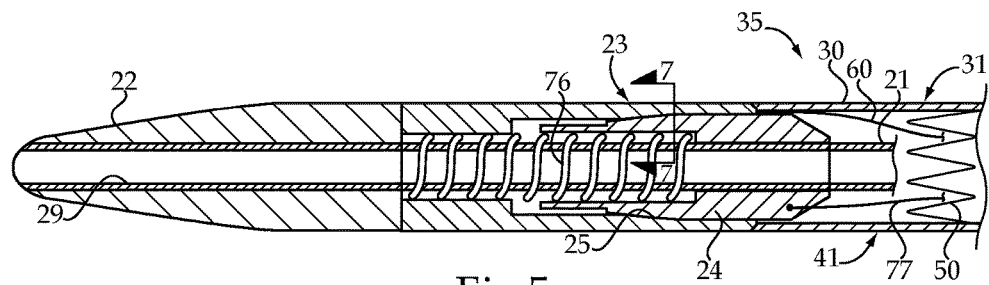
Fig.5
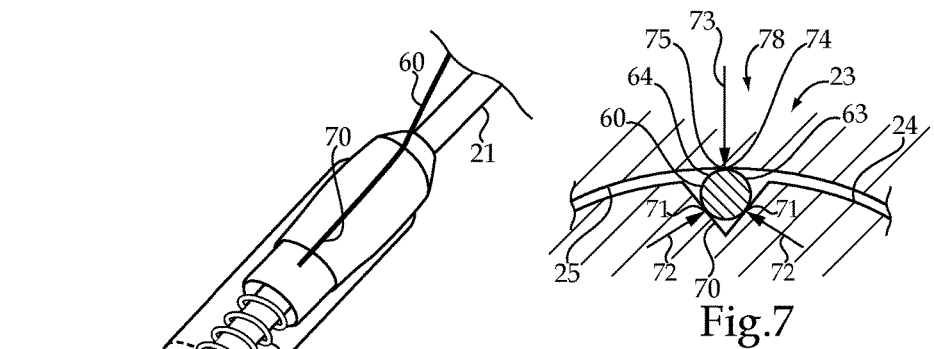
Fig.6
Fig.7
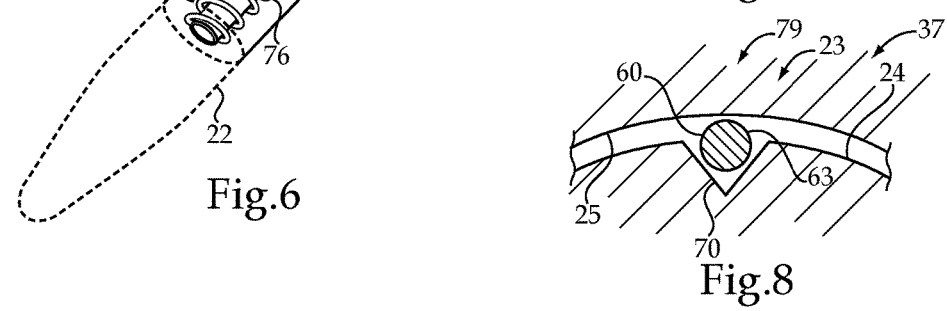
Fig.8
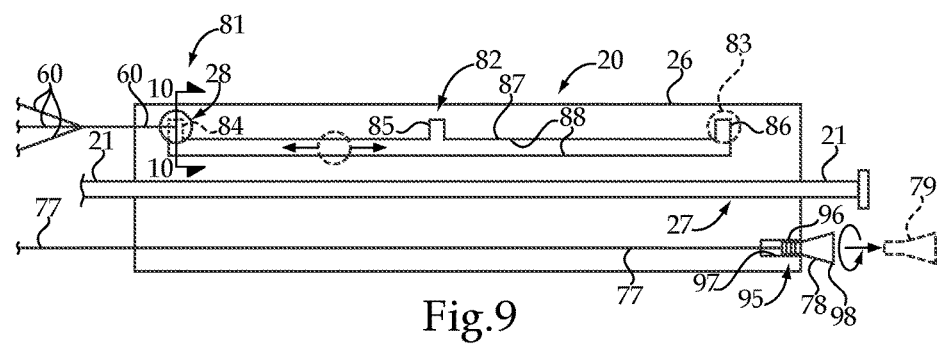
Fig.9
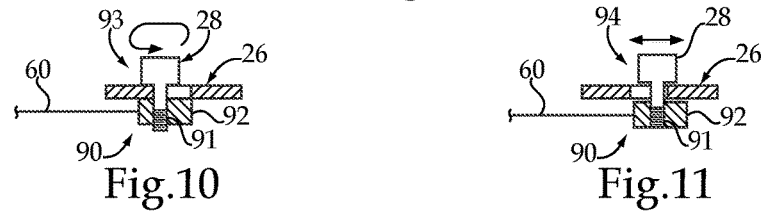
Fig.10  Fig.11

US 10,463,517 B2

CONTROLLED EXPANSION STENT GRAFT DELIVERY SYSTEM

TECHNICAL FIELD

The present disclosure relates generally to stent graft delivery systems, and more particularly to controlled expansion of stent grafts that may have orientation and/or positioning sensitivities.

BACKGROUND

Some variability is involved with placing stent grafts when un-sheathing and allowing full expansion utilizing known self-expanding stent designs. Some stent grafts, such as those located in the aorta, require precise placement and are often delivered by unsheathing the device to a secondary constrained diameter. From this point, the clinician may interpolate the stent graft's likely landing zone, and release the stent graft to self-expand to its final diameter opposed to a vessel wall. This process can introduce variability in a final landing zone due to the jump that occurs between the intermediate and final diameters in which the device is not constrained to the delivery system. During this brief period of time, blood flow and other factors can impact the trajectory of the stent graft changing its final landing zone. Problems can occur when the final landing zone is different from the intended landing zone for the stent graft, either in position or orientation, or both.

The present disclosure is directed toward one or more of the problems set forth above.

SUMMARY

In one aspect, a controlled explanation stent graft delivery system includes a delivery catheter, which defines a longitudinal axis, and includes a tip with a tether clamp. The system also includes a retractable sheath and a stent graft that includes a fabric tube attached to, and supported by, a self expanding stent. A handle is attached to the delivery catheter at an end opposite to the tip. A control tether is attached to an axial movement actuator mounted to the handle. The delivery system has a delivery configuration in which the stent graft is mounted on the delivery catheter in a compressed state and covered by the retractable sheath. The delivery system has an adjustment configuration in which the retractable sheath is at a retracted position out of contact with the stent graft, and the control tether is held by the tether clamp and wrapped around the stent graft, and the axial movement actuator is at a second position with respect to the handle. The delivery system has a release configuration in which the control tether is released from the tether clamp and wrapped around the stent graft, and the stent graft is in an expanded state. The delivery system has a detached configuration in which the stent graft is in the expanded state and the control tether is out of contact with the stent graft. The axial movement actuator is at a first position with respect to the handle in at least one of the delivery configuration and the release configuration.

In another aspect, a method of operating a controlled expansion stent graft delivery system includes positioning the delivery system at a treatment site at a delivery configuration in which the stent graft is mounted on the delivery catheter in a compressed state and covered by the retractable sheath. The delivery system is changed to an adjustment configuration in which the retractable sheath is at a retracted position out of contact with the stent graft, and the control tether is held by the tether clamp and wrapped around the stent graft, and the axial movement actuator is at a second position with respect to the handle. The delivery system can be changed to a release configuration in which the control tether is released from the tether clamp and wrapped around the stent graft, and the stent graft is in an expanded state. The delivery system is changed to a detached configuration in which the stent graft is in the expanded state and the control tether is out of contact with the stent graft. The axial movement actuator is at a first position with respect to the handle in at least one of the delivery configuration and the release configuration.

BRIEF DESCRIPTION OF THE DRAWINGS

FIG. 1 is an enlarged side view of a stent graft and control tether assembly mounted on the delivery system, which is partially shown;

FIG. 2 is a sectioned view through the assembly of FIG. 1 as viewed along section lines 2-2;

FIG. 3 is a schematic view of the control tether being tensioned between reduced and enlarged diameter configurations;

FIG. 4 is a close up perspective view through one of the loops of FIG. 1;

FIG. 5 is an enlarged schematic sectioned view of the tip of a delivery catheter for the delivery system of FIG. 1;

FIG. 6 is an enlarged see-through perspective view of the tip region of the delivery system of FIG. 1;

FIG. 7 is a partial sectioned view through the tether clamp of FIG. 5 in a clamped position;

FIG. 8 is a partial sectioned view of through the tether clamp in a release position;

FIG. 9 is a schematic view of a handle for the delivery system of FIG. 1;

FIG. 10 is a schematic section view through the axial movement actuator and a portion of the handle along section lines 10-10 of FIG. 9;

FIG. 11 is a schematic section view similar to FIG. 10 except showing the axial movement actuator unlocked for movement;

DETAILED DESCRIPTION

Figure 12:
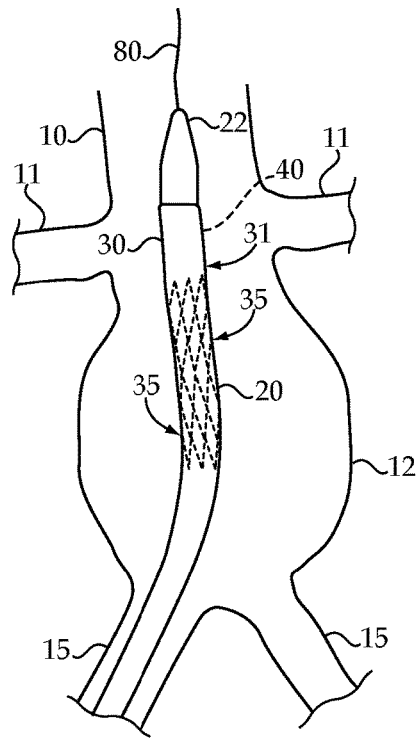
FIG. 12 is a schematic view of a controlled expansion stent graft delivery system being maneuvered through an aorta in a delivery configuration.

Referring initially to FIGS. 1-11, a controlled expansion stent graft delivery system 20 is utilized to deliver a stent graft 40 to a treatment location in a patient. In the illustrated embodiment, stent graft 40 includes a fabric tube 45 that is attached to, and supported by, a self expanding stent 46, and is shaped for treatment of an abdominal aortic aneurism in a manner known in the art. Stent graft 40 is a portion of an assembly 50 that includes at least one control tether 60.

Apart from a stent graft and control tether assembly 50, the delivery system 20 includes a delivery catheter 21 with a tip 22 that includes a tether clamp 23. A retractable sheath 30 is slidably movable with regard to the delivery catheter 21 in a manner well known in the art. In addition to the sutures that may or may not be included to attach the fabric tube 45 to the self expanding stent 46, the stent graft 40 includes a plurality of loops 47 that are attached to at least one of the fabric tube 45 and the self expanding stent 46. Loops 47 may be formed with suture material. Each of the loops 47 has an opening 48 exposed on a radially outward side 49 of fabric tube 45. Each of three control tether(s) 60 in the illustrated embodiment includes a first segment 65, a middle segment 66 and a second segment 67. Each middle segment 66 is wrapped around the fabric tube 45 and is received through the respective openings 48 of the loops 47 at each of three different longitudinal positions along stent graft 40. The first segment 65 of each of the control tethers 60 extends beyond one end 51 of the fabric tube 45. Each of the second segments 67, which are longer than the respective first segments 65, extends beyond an opposite end 52 of the fabric tube 45.

As partially shown in FIG. 5, delivery system 20 has a delivery configuration 35 in which the stent graft 40 is mounted on the delivery catheter 21 in a compressed state 41 and covered by the retractable sheath 30, which is at a covering position 31. The delivery system 20 is movable from the delivery configuration 35 shown in FIG. 5 to an adjustment configuration 36 (FIGS. 13-15) in which tension in the control tether(s) 60 keeps the stent graft 40 from fully expanding to allow the user to adjust a position and/or an orientation of the stent graft 40 in-vitro. The delivery system 20 may be moved from the adjustment configuration 36 to a release configuration 37 (FIG. 8) with the stent graft in an expanded state 42 after the positioning and orientation of the stent graft 40 have been adjusted by the user to a desired landing zone in the treatment vessel. The release configuration is characterized by the control tether 60 being released from tether clamp 23 but still wrapped around stent graft 40. Thereafter, the delivery system 20 may be movable from the release configuration 37 to a detached configuration 30 in which the stent graft 40 is in the expanded state 42 and the control tether(s) 60 is pulled toward handle 26 and out of contact with the stent graft 40. Thus, the use of the control tether(s) 60 allows the user to controllably expand, shrink and re-expand the stent graft 40 in-vitro to better position the stent graft 40 at a desired position and orientation within a patient.

In the example embodiment shown in FIGS. 1 and 2, stent graft 40 includes a first set 57 of three loops 47 located at a first longitudinal location 33, and a second set 58 of at least three loops 47 at a second longitudinal location 34 that is spaced along the longitudinal axis from the first set of loops 57. In addition, a third set of at least three loops 47 is located at a longitudinal position between the first longitudinal location 33 and the second longitudinal location 34. Although each longitudinal location has three loops 47, one, two or four or more loops at each location would also fall within the scope of this disclosure. These spaced apart longitudinal positions are chosen such that when the tension is applied to the control tethers 60, the respective middle segments 66 can be used to change the self expanding stent 46 between a reduced diameter configuration 55 (FIG. 3) when the control tether(s) 60 is in tension, and an enlarged diameter configuration 56 (FIGS. 1-3) when the control tether(s) 60 has little or no tension. As best shown in FIG. 4, the opening 48 defined by each of the loops 47 is at least several times larger than the diameter 68 of the respective control tether 60 so that the control tether 60 is freely slidable through the respective opening 48. In the illustrated embodiment, the loops 47 have been shown added to a conventional AAA bifurcated main body graft of the type manufactured by Cook Inc., but the present disclosure is also applicable to stent grafts for virtually any treatment application, especially those requiring precise placement and orientation. Each of the respective control tethers 60 is received through one of the loops 53 in the respective set of loops 57 or 58 exactly twice and received through the other loops 54 of that respective set of loops exactly once. This feature is shown for example in FIG. 2, and partially shown in FIGS. 1, 3 and 4.

When delivery system 20 is in either the delivery configuration 35 (FIG. 12) and an adjustment configuration 36 (FIGS. 13-15) to be described infra, the first segment 65 of each of the respective control tethers 60 is held by the tether clamp 23, which forms a portion of tip 22. Thus, by jailing first segments 65, a user can apply tension to the remote end of second segment 67 by moving an axial movement actuator 28 mounted to move on the handle 26, to control shrinkage and expansion of the stent graft 40 between the reduced diameter configuration 55 and the enlarged diameter configuration 56. The stent graft 40 changes its diameter responsive to a tension level in the control tether(s) 60 when the delivery system 20 is in its adjustment configuration 36. The user may actually reduce the diameter of stent graft 40 responsive to an increase in the tension level of the control tether(s) 60 when the delivery system 20 is in the adjustment configuration 36. The tension level in the control tether 60 acts in opposition to the spring tendency of the self expanding stent 46 to expand.

Referring now specifically to FIGS. 9-11, the delivery system 20 includes a handle 26 attached to delivery catheter 21 at an end 27 opposite to the tip 22. The remote end of control tether(s) 60 is attached to an axial movement actuator 28 mounted to handle 26. The axial movement actuator 28 is constrained to move within a guiding slot 87 that include guide surfaces defined by portions of handle 26. Guide slot 87 may be aligned with the longitudinal axis of catheter 21. In the illustrated embodiment, the axial movement actuator 28 can be stopped in perpendicularly oriented notches 84, 85 and 86, which correspond to different positions. For instance, the delivery system could initially be set up with the axial position actuator 28 in the notch 84 corresponding to a first position 81 such that the control tether(s) 60 would not interfere with full radial expansion of the stent graft 40 at time of implantation. However, if the stent graft 40 lands at an undesirable location or orientation, the user may then move the axial movement actuator 28 toward notches 85 or 86 (adjustment configuration 36) in order to apply tension to control tether(s) 60 to reduce the diameter of the stent graft 40 to make it possible to readjust at least one of its position and orientation at the implantation site. Thereafter the user can again move the axial position actuator 28 toward the first notch 84 in order to allow for full expansion of the stent graft 40 at the new landing location. The axial position actuator 28 may include a position lock 90 so that the axial position actuator can be locked into one of the notches 84-86, or maybe even at a desired location in guide slot 87. This may be accomplished by a threaded end 91 of the axial position actuator 28 being threadably received in a block 92, with a wall of the handle 26 sandwiched therebetween. By tightening threads 91 into block 92, the wall of the handle 26 can be clamped therebetween to hold the control tether 60 in a desired placement and tension state, corresponding to the position lock 90 being in a locked state. By untightening threads 91 from block 92 the position lock is placed in a unlocked state, and the axial position actuator 28 may be moved to any desired location constrained by guide slot 87, and then may be stopped at that new location by again locking position lock 90. The remote end of control tether 60 may be attached to move with block 92 as shown in FIGS. 10 and 11.

Position lock 90 could take on other forms and structures known in the art for allowing and locking against relative movement in medical devices. Although FIG. 9 shows the axial position actuator 28 initially positioned at a first position in notch 84, the system could also be set up initially to have the axial position actuator in an optional initial position 83 corresponding to notch 86. In such a case, the control tether 60 would initially be in tension to prevent the stent graft 40 from fully expanding after the retractable sheath 30 is moved to its retracted position 32. In such an instance, the operator could then manipulate the delivery system and the control tether via the axial movement actuator 28 to controllably land the stent graft 40 at a desired location and orientation at a delivery site. Thus, the delivery system 20 of the present disclosure can be set up initially to allow the operator to only use the control tethers if the stent graft 40 lands at an undesirable location or orientation, or may allow the user to control the expansion of the stent graft 40 prior to any landing.

A remote end of the clamp release line 77 may be attached to a clamp release lock 95 such that the clamp release line 77 extends between the tether clamp 23 (FIG. 5) and the handle 26 (FIG. 9). In the illustrated embodiment, clamp release lock 95 operates by including a threaded end 96 received in a threaded bore 97 defined by handle 26. Thus, when the clamp release lock 95 is threadably received in threaded bore 97 as shown in FIG. 9, the clamp release actuator 98 is inoperable. FIG. 9 also shows the dotted lines after the clamp release actuator 95 has been unthreaded from threaded bore 97 and moved backwards to move the tether clamp 23 from its clamped position 78 to the release position 79. Numerals 78 and 79 appear in FIGS. 7-9 to show the relationship between clamp release actuator 98 and the positioning of tether clamp 23. Movement of the tether clamp may be enabled by unthreading clamp release actuator 98 from threaded bore 97 in handle 26 to allow the clamp release actuator to be moved away from handle 26 to move the tether clamp to its release position 79. When a tether clamp 23 is in the release configuration 79, the axial movement actuator 28 may be moved in the direction of notch 86 to move the remote end of control tether 60 away from tether clamp 23.

Other clamp release lock structures would also fall within the intended scope of this disclosure. Although the illustrated embodiment shows the tether clamp 23 being moved to a release position 79 by pulling on a clamp release line 77, the present disclosure also contemplates an alternative. For instance, a cannula may be mounted about delivery catheter 21 and operable slid to a compression position in contact with tether clamp 23 to cause the same to release. In such an alternative, the remote end of the cannula adjacent handle 26 might include a clamping feature to require that the cannula be unclamped from catheter 21 before the clamp release function is made operable by movement of the cannula.

Although tether clamp 23 can take on a wide variety of different forms, in the illustrated embodiment as best shown in FIGS. 5-8, the illustrated tether clamp 23 includes a male part 24 that is mated to a female part 25. In the illustrated embodiment, tether clamp 23 includes a tension spring 76 that is operably positioned to bias the male part 24 and the female part 25 toward a clamped position 78 as shown in FIG. 7. Those skilled in the art will appreciate that the spring could be a compression spring with an appropriate re-arrangement of the male and female portions of the tether claim without departing from the present disclosure. A clamp release line 77 may be connected to tether clamp 23 in general, and in the illustrated embodiment to the male part 24 in particular. The tether clamp 23 can move from the clamped position as shown in FIG. 7 toward a release position 79 as shown in FIG. 8 responsive to tension in the clamp release line 77 overcoming the bias of spring 76. Thus, after the stent graft 40 is precisely placed, the tether clamp 23 can be moved to its release position 79 to allow the control tether(s) 60 to be withdrawn toward a handle 26 of delivery system 20 and out of contact with stent graft 40. In the illustrated embodiment, the three control tethers 60 are shown as merged into a single control tether 60 before attachment to axial movement actuator 28 so that the three control tethers 60 shown in FIG. 1 can be simultaneously tensioned and un-tensioned responsive to movement of axial movement actuator 28 and the remote end of the control tether 60 relative to handle 26 as shown in FIG. 9. The user may increase or decrease tension in the control tether(s) 60 and allow the self expanding stent 46 to pull the control tether 60 toward stent graft 40, or in a reverse direction to increase tension against the action of the self expanding stent 46.

Although not necessary, each control tether 60 may be a monofilament wire 63, with the tether clamp 23 constructed to contact the monofilament wire 63 at three spaced apart locations 73 around a circumference 64 of the monofilament wire 63 as best shown in FIG. 7. In order to have the three point clamping configuration as shown in FIG. 7, one of the male part 24 and the female part 23 defines a v-shaped groove 70 that includes two of three clamping surfaces 71 that contact the monofilament wire 63 at two of three spaced apart locations 73. The other one of the male part 24 and female part 25 includes a clamping surface 74 that contacts the monofilament wire 63 at a remaining one 75 of the three spaced apart locations 73. Those skilled in the art will appreciate that other clamping configurations could be utilized, and the control tether(s) could be multifilament instead of the monofilament wire 63 of the illustrated embodiment.

Figure 17:
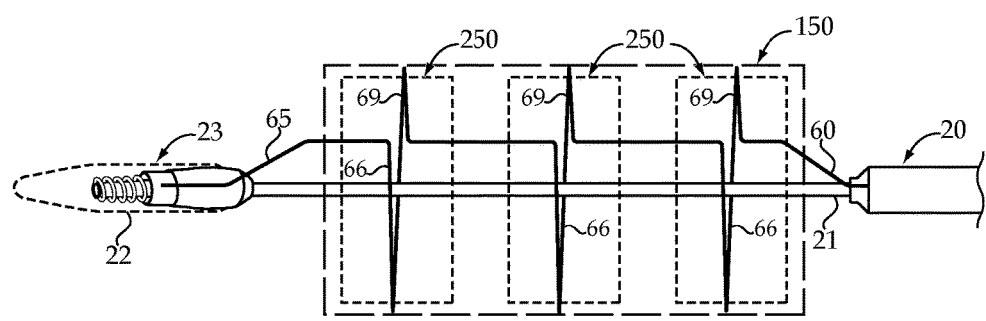
FIG. 17 is a schematic view of two more version of delivery system according to the present disclosure.

Referring now in addition to FIG. 17, a couple of different variations of a stent graft and control tether assembly 150 and 250 are shown. With regard to assembly 150, a single stent graft is schematically shown and has a single control tether 60 wrapped around the stent graft so that middle segment 66 wraps around the fabric tube a first time and a second time 69 and the third time, thus illustrating that each control tether may wrap around an individual stent graft more than one time at different longitudinal locations along the stent graft. Also shown, is an assembly 250 in which three separate stent grafts share a common single control tether 60 such that each of the three stent grafts has a middle segment 66 of the control tether 60 wrapped one time around each of the three stent grafts. Thus, those skilled in the art will appreciate that the present disclosure is applicable to delivery assemblies for delivering more than one stent graft that share a common control tether and to a single stent graft that uses only one control tether wrapped around the stent graft more than one time. This is to be contrasted with the illustrated embodiment in which three control tethers 60 are used with each of the control tethers 60 being wrapped around the stent graft 40 one time. Those skilled in the art will appreciate that other permutations would also fall within the scope of this disclosure.

INDUSTRIAL APPLICABILITY

The present disclosure finds general applicability to any self expanding stent graft. The present disclosure finds particular applicability to stent grafts with sensitivities to placement location and/or orientation, such as for accommodating branch vessels. The present disclosure finds specific applicability for delivering stent grafts to high flow areas, such as those associated with the aorta, which also include many branching arteries that must be accommodated by proper placement and orientation of a stent graft.

Figure 13:
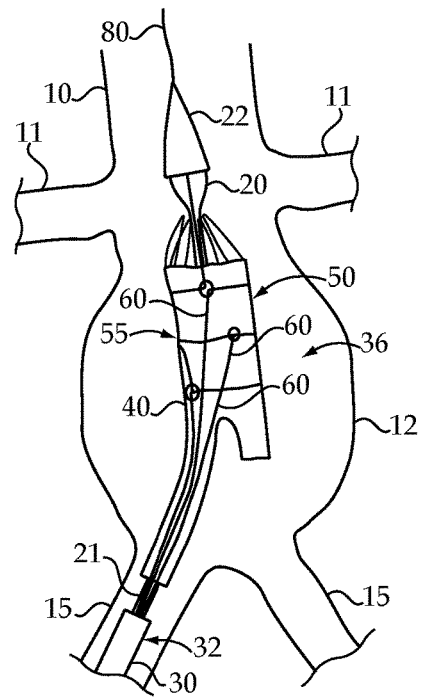
FIG. 13 shows the delivery system moved from the delivery configuration of FIG. 10 to an adjustment configuration.
Figure 14:
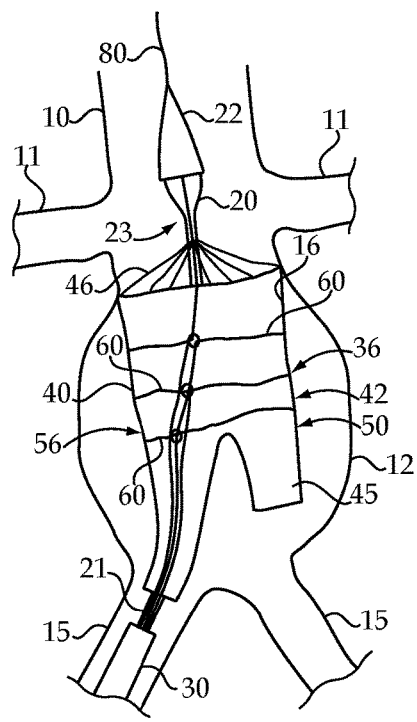
FIG. 14 is a schematic view of the delivery system in the adjustment configuration with the stent graft expanded.
Figure 15:
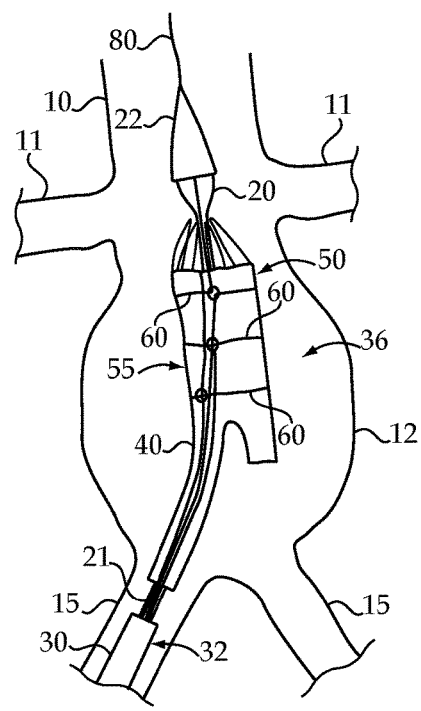
FIG. 15 is a schematic view of the delivery system an adjustment configuration with the stent graft partially expanded.

Referring now in addition to FIGS. 12-16, an example method of operating a controlled expansion stent graft delivery system 20 is shown for treating an aneurysm 12 in the aorta 10 that is located immediately below branching vessels, which may include the renal artery 11. The delivery system 20 may approach the implantation site utilizing a previously placed wire guide 80 utilizing an access in the patient's leg (not shown) and travel up through the iliac artery 15. Wire guide 80 may be received through a lumen 29 of delivery catheter 21. In particular, the delivery system 20 is positioned at a treatment site in a delivery configuration 35 in which the stent graft 40 is mounted on delivery catheter 21 in a compressed state 41 and covered by retractable sheath 30, which is at a covering position 31. Next, as shown in FIG. 13, the delivery system is moved to the adjustment configuration 36 with the retractable sheath 30 moved from the covering position 31 shown in FIG. 10 to the retracted position 32 to uncover the stent graft 40. Because the stent graft 40 did not fully expand upon retraction of retractable sheath 30, this reveals that the control tether(s) 60 were configured with some initial tension by initially positioning axial position actuator 28 in notch 86 or in notch 85 depending upon the total movement length available for control tether 60 in a given diametrical application. When in the adjustment configuration 36, the control tethers 60 have sufficient tension to prevent the stent graft 40 from fully expanding. When in this configuration, the retractable sheath 30 is out of contact with the stent graft 40. However, the control tethers 60 are held by the tether clamp 23, are wrapped around the stent graft 40, and received through the openings 48 in the individual loops 47 of the stent graft 40. The delivery system 20 may be changed from the delivery configuration of FIG. 12 to the adjustment configuration 36, thus allowing the user to make some orientation change via rotating delivery system 20 about its longitudinal axis and positioning adjustments by advancing or retracting the delivery system 20 with regard to the aneurysm 12. When the user believes that the stent graft 40 is properly positioned, tension on the control tethers 60 may be relaxed by unlocking position lock 90 and moving axial position actuator toward notch 84, and allow the self expanding stent 46 to move the stent graft 40 into contact with the vessel wall at an initial landing zone 16. The user can then use known visualization strategies to assess both the orientation and placement of stent graft 40 while the delivery system 20 is still in an adjustment configuration 36. The difference between the adjustment configuration 36 shown in FIG. 13 and that shown in FIG. 14 is associated with the level of tension in the control tether(s) 60 via the positioning of axial movement actuator 29. If the physician deems that the initial landing zone 16 is not acceptable, the tension level in the control tethers 60 may be increased to shrink the diameter of stent graft 40 as shown in FIG. 15.

Figure 16:
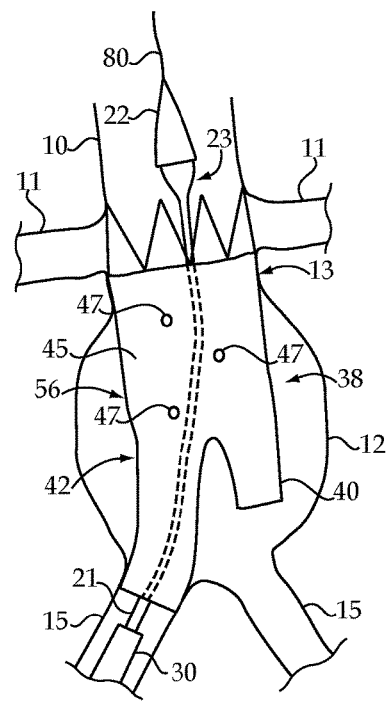
FIG. 16 is a schematic view of the delivery system of FIG. 10 in a detached configuration.

When in the adjustment configuration 36, the user may adjust the orientation and position of the stent graft 40, and then relieve tension on the control tether(s) 60 so that the stent graft 40 is controllably expanded to the desired landing zone 13 as shown in FIG. 16. After confirming the proper placement of stent graft 40, the physician may release the top stent proximal fixation that are adjacent the renal artery 11 in a manner well known in the art. Next, after confirming a proper seal, the delivery system 20 may be moved from the adjustment configuration 36 to a release configuration 37 (FIG. 8) in which the control tether 60 is released from the tether clamp 23, but remains wrapped around the stent graft 40 and received through the openings 48 of the loops 47, and the stent graft 40 is in its expanded state 42. Changing to the release configuration may include movement of the clamp release lock 95 to an un-locked state by unthreading clamp release actuator 98 from threaded bore 97. Next, the clamp release actuator is moved away from handle 26 as shown in FIG. 9 to move tether clamp 23 to its release position 79. When this is done, the axial movement actuator 28 may be moved slightly to move the remote end of control tether 60 out of tether clamp 23 so that when the tether clamp 23 returns toward its clamp position under the action of spring 76, the control tether 60 is no longer present. This movement moves the clamp release line 77 to move the clamp 23 from the clamp position 78 shown in FIG. 7 to the unclamped positioned 79 shown in FIG. 8.

Thereafter, the delivery system 20 may then be moved from the release configuration 37 to a detached configuration 38 as shown in FIG. 16 in which the stent graft 40 is at the expanded state 42 and the control tether 60 is slid out of contact with the stent graft 40. This is accomplished because the first segment 65 of the individual control tether(s) have been released from tether clamp 23, and withdrawn back through loops 47 toward handle 26 and out of contact with the stent graft 40. Next, the user may withdraw the delivery system 20 leaving the stent graft 40 implanted in a desired position and orientation.

Those skilled in the art will appreciate that while the delivery system 20 is in the adjustment configuration 36 as shown in FIGS. 13-15, the expansion of stent graft 40 may be stopped by increasing tension in the control tether(s) 60. The user may then adjust at least one of the orientation and position of the stent graft 40 while expansion of the stent graft 40 has been stopped. Thereafter, the expansion of the stent graft may be controllably resumed by decreasing tension in control tether 60. The expansion of the stent graft 40 may be stopped by securing the axial movement actuator 28 at any desired position using position lock 90. If the positioning and/or orientation are not as desired, the stent graft 40 may be contracted toward the compressed state 41 by increasing tension in the control tether 60 while the delivery system 20 is in the adjustment configuration 36. As discussed earlier, after proper placement, the tether clamp 23 may be moved from its clamped position 78 to its release position 79 responsive to increasing tension in the clamped release line 77.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:
1. A controlled expansion stent graft delivery system comprising:

a delivery catheter with a tip that includes a tether clamp, and defining a longitudinal axis;
a retractable sheath;
a stent graft that includes a fabric tube attached to, and supported by, a self expanding stent;
a handle attached to the delivery catheter at an end opposite to the tip;
a control tether attached to an axial movement actuator mounted to the handle;
the delivery system having a delivery configuration in which the stent graft is mounted on the delivery catheter in a compressed state and covered by the retractable sheath;
the delivery system having an adjustment configuration in which the retractable sheath is at retracted position out of contact with the stent graft; and the control tether is held by the tether clamp, wrapped completely around the longitudinal axis at a radially outward side of the fabric tube, and the axial movement actuator is at a second position with respect to the handle;
the delivery system having a release configuration in which the control tether is released from the tether clamp, wrapped around the stent graft, and the stent graft is in an expanded state;
the delivery system having a detached configuration in which the stent graft is in the expanded state and the control tether is out of contact with the stent graft; and
the axial movement actuator is at a first position with respect to the handle in at least one of the delivery configuration and the release configuration.

2. The delivery system of claim 1 wherein the axial movement actuator is at the first position with respect to the handle when the delivery system is in the release configuration; and
the expansion state of the stent graft being greater when the axial movement actuator is in the first position versus the second position.

3. The delivery system of claim 1 wherein the axial movement actuator is at the first position with respect to the handle when the delivery system is in the delivery configuration;
the expansion state of the stent graft being greater when the axial movement actuator is in the second position versus the first position.

4. The delivery system of claim 1 including a position lock moveable between an unlocked state at which the axial movement actuator can move away from one of the first position and the second position, and a locked state at which the axial movement actuator is locked at the one of the first position and the second position.

5. The delivery system of claim 1 including a clamp release line extending between the tether clamp and the handle, and being moveable between a clamp position at which the tether is held by the tether clamp, and a release position at which control tether is released from the tether clamp.

6. The delivery system of claim 1 wherein the tether clamp includes a spring operably positioned to bias the tether clamp toward a clamp position.

7. The delivery system of claim 1 including a clamp release lock positioned closer to the handle than to the tip, and being moveable between a first position at which a clamp release actuator is inoperable, and a second position at which the clamp release actuator is operable to move the tether clamp from a clamp position toward a release position.

8. The delivery system of claim 7 wherein the tether clamp includes a spring operably positioned to bias the tether clamp toward the clamp position; and
a clamp release line extending between the tether clamp and the handle, and being moveable between the clamp position at which the tether is held by the tether clamp, and the release position at which tether is released from the tether clamp.

9. The delivery system of claim 8 wherein the handle includes a longitudinal guide surface oriented parallel to the longitudinal axis; and
the guide surface constrains the axial movement actuator between the first position and the second position.

10. The delivery system of claim 9 including a position lock moveable between an unlocked state at which the axial movement actuator can move away from the second position, and a locked state at which the axial movement actuator is locked at the second position.

11. The delivery system of claim 10 wherein the axial movement actuator is at the first position with respect to the handle when the delivery system is in the release configuration; and
the expansion state of the stent graft being greater when the axial movement actuator is in the first position versus the second position.

12. The delivery system of claim 11 wherein the axial movement actuator is at the first position with respect to the handle when the delivery system is in the delivery configuration;
the expansion state of the stent graft being greater when the axial movement actuator is in the second position versus the first position.

13. A method of operating a controlled expansion stent graft delivery system that includes a delivery catheter with a tip that includes a tether clamp, and defining a longitudinal axis; a retractable sheath; a stent graft that includes a fabric tube attached to, and supported by, a self expanding stent; a handle attached to the delivery catheter at an end opposite to the tip; a control tether attached to an axial movement actuator mounted to the handle, and the method comprising the steps of:
positioning the delivery system at a treatment site in a delivery configuration in which the stent graft is mounted on the delivery catheter in a compressed state and covered by the retractable sheath;
changing the delivery system to an adjustment configuration in which the retractable sheath is at retracted position out of contact with the stent graft; and the control tether is held by the tether clamp, wrapped completely around the longitudinal axis at a radially outward side of the fabric tube, and the axial movement actuator is at a second position with respect to the handle;
changing the delivery system to a release configuration in which the control tether is released from the tether clamp, wrapped around the stent graft, and the stent graft is in an expanded state; and
changing the delivery system to a detached configuration in which the stent graft is in the expanded state and the control tether is out of contact with the stent graft; and
the axial movement actuator is at a first position with respect to the handle in at least one of the delivery configuration and the release configuration.

14. The method of claim 13 including stopping expansion of the stent graft by positioning the axial movement actuator at the second position while the delivery system is in the adjustment configuration;

adjusting at least one of an orientation and a position of the stent graft while the expansion of the stent graft is stopped; and resuming expansion of the stent graft by decreasing tension in the control tether by moving the axial adjustment actuator away from the second position.

15. The method of claim 13 including partially expanding the stent graft by moving the axial movement actuator from the first position to the second position when changing from the delivery configuration to the adjustment configuration.

16. The method of claim 13 including contracting the stent graft toward the compressed state by moving the axial movement actuator.

17. The method of claim 14 including adjusting at least one of an orientation and a position of the stent graft after contracting the stent graft toward the compressed state; and resuming expansion of the stent graft by decreasing tension in the control tether by moving the axial movement actuator.

18. The method of claim 13 including locking the axial movement actuator at one of the first position and the second position by moving a position lock from an unlocked state to a locked state.

19. The method of claim 13 including a step of moving the tether clamp from a clamp position to a release position by moving a clamp release line with respect to the handle.

20. The method of claim 13 including enabling operation of a clamp release actuator by moving a clamp release lock from a first position to a second position at which the clamp release actuator is operable to move the tether clamp from a clamp position toward a release position.

\* \* \* \* \*